US012678220B2

(12) United States Patent
Rodriguez et al.

(10) Patent No.: US 12,678,220 B2
(45) Date of Patent: Jul. 14, 2026

(54) COUPLERS, STRAIN RELIEF HUBS, AND NOSE PIECES FOR AN ABLATION CATHETER ASSEMBLY AND METHODS OF USING THE SAME

(71) Applicant: Biosense Webster (Israel) Ltd., Yokneam (IL)

(72) Inventors: Jasson Rodriguez, Irvine, CA (US); Audrey Vu, Irvine, CA (US); Roozbeh Borjian, Irvine, CA (US); SR Prasad, Irvine, CA (US); Anabel Haro, Irvine, CA (US); Amie Kim, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 684 days.

(21) Appl. No.: 18/056,580

(22) Filed: Nov. 17, 2022

(65) Prior Publication Data

US 2023/0200894 A1    Jun. 29, 2023

Related U.S. Application Data

(60) Provisional application No. 63/293,469, filed on Dec. 23, 2021.

(51) Int. Cl.
| | |
|---|---|
| *A61B 18/14* | (2006.01) |
| *A61B 18/00* | (2006.01) |
| *A61M 25/10* | (2013.01) |

(52) U.S. Cl.
CPC ..... *A61B 18/1492* (2013.01); *A61M 25/1025* (2013.01); *A61B 2018/00172* (2013.01);
(Continued)

(58) Field of Classification Search
CPC ........ A61B 18/1492; A61B 2018/0022; A61B 2018/00613; A61B 2018/1467;
(Continued)

(56) References Cited

U.S. PATENT DOCUMENTS

| | | | |
|---|---|---|---|
| 5,378,238 A | 1/1995 | Peters et al. | |
| 5,637,086 A * | 6/1997 | Ferguson | .............. A61M 25/10 |
| | | | 604/509 |

(Continued)

FOREIGN PATENT DOCUMENTS

| | | |
|---|---|---|
| EP | 1118348 A2 | 7/2001 |
| EP | 1009473 B1 | 11/2005 |

(Continued)

OTHER PUBLICATIONS

Partial Search Report dated May 22, 2023, from Corresponding EP Application No. 22215930.3.

(Continued)

*Primary Examiner* — Joseph A Stoklosa
*Assistant Examiner* — Marina Delaney Templeton

(57) ABSTRACT

The disclosed technology includes couplers, nose pieces, and strain relief hubs for ablation catheter assemblies and methods of using the same. The disclosed technology can include a medical probe having a coupler having a first portion, a second portion, and a vent port. The second portion can slide between a first position and a second position. When in the first position, the vent port can be at least partially obstructed by the first portion and, when in the second position, the vent port can be unobstructed by the first portion. The medical probe can include a nose piece having an outer diameter of less than 0.14 inches and an aperture extending therethrough. The aperture can be sized to receive a catheter. The medical probe can include a strain relief hub having a first portion and a second portion and configured to be coupled to a handle of the medical probe.

15 Claims, 14 Drawing Sheets

(52) U.S. Cl.
CPC ................. *A61B 2018/0022* (2013.01); *A61B 2018/00613* (2013.01); *A61B 2018/1467* (2013.01); *A61M 2025/1077* (2013.01)

(58) Field of Classification Search
CPC .. A61B 2018/1465; A61B 2018/00214; A61B 2018/0091; A61M 25/1018; A61M 25/10184; A61M 25/10185; A61M 25/10186; A61M 25/1025; A61M 25/0097; A61M 25/0075; A61M 25/10; A61M 2025/0098; A61M 2025/0681; A61M 39/22
See application file for complete search history.

(56) References Cited

U.S. PATENT DOCUMENTS

| | | | | | |
|---|---|---|---|---|---|
| 2004/0181189 | A1* | 9/2004 | Roychowdhury | .... | A61M 25/10 |
| | | | | | 604/96.01 |
| 2006/0263145 | A1* | 11/2006 | Pal | ........................... | A61F 2/95 |
| | | | | | 403/1 |
| 2008/0177130 | A1 | 7/2008 | Vijay | | |
| 2011/0125132 | A1* | 5/2011 | Krolik | ............. | A61M 25/10185 |
| | | | | | 604/509 |
| 2012/0197193 | A1* | 8/2012 | Krolik | ................... | A61B 5/6853 |
| | | | | | 604/99.04 |
| 2013/0060236 | A1 | 3/2013 | Ogle | | |
| 2013/0116651 | A1* | 5/2013 | Takagi | ............... | A61M 25/0054 |
| | | | | | 604/525 |
| 2017/0245930 | A1* | 8/2017 | Brannan | ............ | A61B 18/1815 |
| 2020/0359996 | A1* | 11/2020 | Walsh | ................ | A61B 17/3478 |

FOREIGN PATENT DOCUMENTS

| | | |
|---|---|---|
| EP | 2777740 A2 | 9/2014 |
| EP | 3616743 A1 | 3/2020 |
| EP | 3906875 A1 | 11/2021 |
| FR | 2650957 A1 | 2/1991 |

OTHER PUBLICATIONS

Extended European Search Report and Opinion dated Jul. 24, 2023, from Corresponding EP Application No. 22215930.3.

* cited by examiner

SECTION X-X

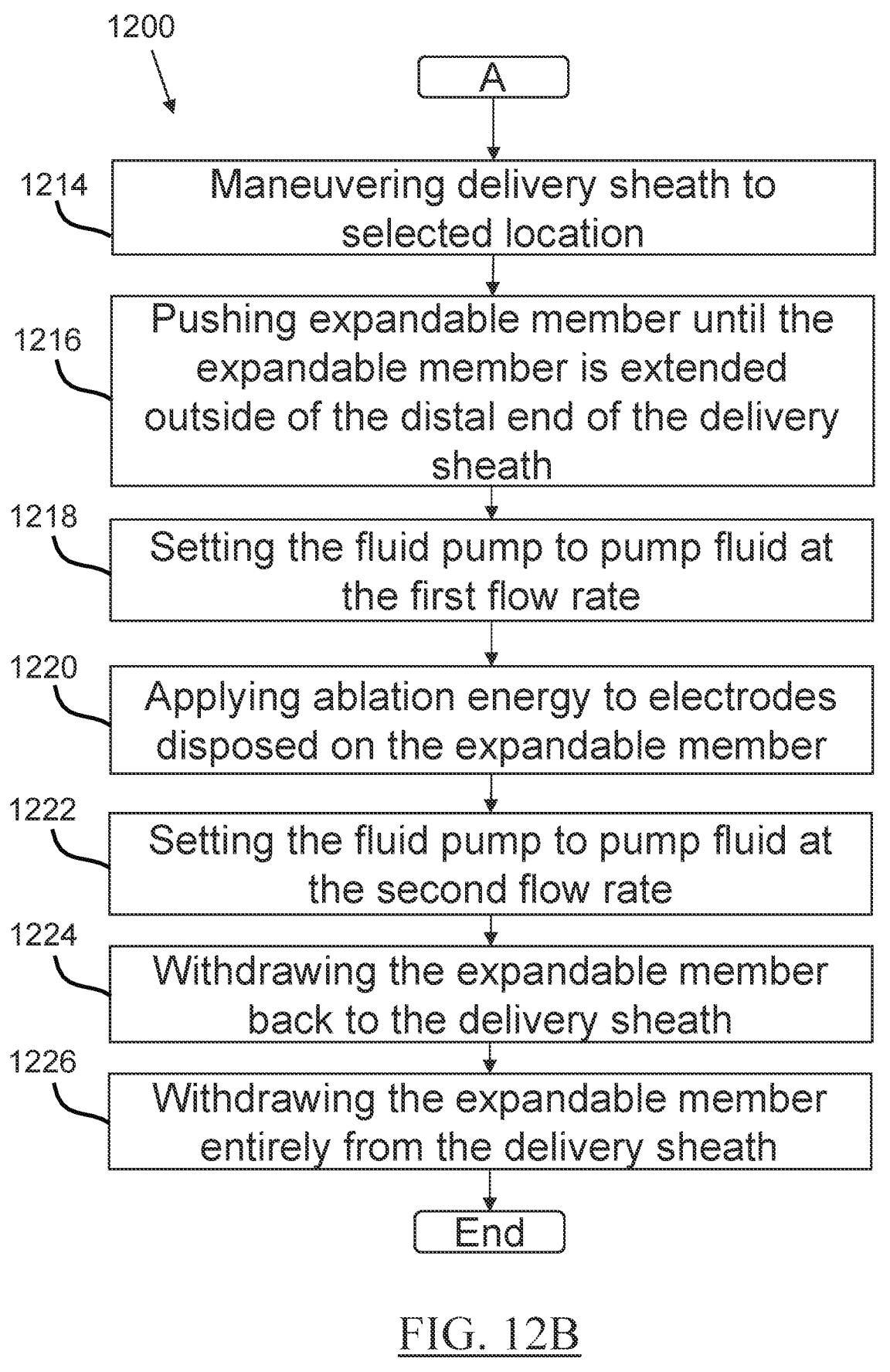

1200

```
                          ┌─────────┐
                          │    A    │
                          └─────────┘
                               │
                               ▼
   ┌──────────────────────────────────────────────────────┐
1214│         Maneuvering delivery sheath to                │
   │              selected location                         │
   └──────────────────────────────────────────────────────┘
                               │
                               ▼
   ┌──────────────────────────────────────────────────────┐
1216│   Pushing expandable member until the                │
   │   expandable member is extended                        │
   │   outside of the distal end of the delivery            │
   │   sheath                                               │
   └──────────────────────────────────────────────────────┘
                               │
                               ▼
   ┌──────────────────────────────────────────────────────┐
1218│   Setting the fluid pump to pump fluid at             │
   │              the first flow rate                       │
   └──────────────────────────────────────────────────────┘
                               │
                               ▼
   ┌──────────────────────────────────────────────────────┐
1220│   Applying ablation energy to electrodes             │
   │   disposed on the expandable member                    │
   └──────────────────────────────────────────────────────┘
                               │
                               ▼
   ┌──────────────────────────────────────────────────────┐
1222│   Setting the fluid pump to pump fluid at             │
   │            the second flow rate                        │
   └──────────────────────────────────────────────────────┘
                               │
                               ▼
   ┌──────────────────────────────────────────────────────┐
1224│   Withdrawing the expandable member                  │
   │        back to the delivery sheath                     │
   └──────────────────────────────────────────────────────┘
                               │
                               ▼
   ┌──────────────────────────────────────────────────────┐
1226│   Withdrawing the expandable member                  │
   │     entirely from the delivery sheath                  │
   └──────────────────────────────────────────────────────┘
                               │
                               ▼
                          ┌─────────┐
                          │   End   │
                          └─────────┘
```

FIG. 12B

COUPLERS, STRAIN RELIEF HUBS, AND NOSE PIECES FOR AN ABLATION CATHETER ASSEMBLY AND METHODS OF USING THE SAME

CROSS REFERENCE TO RELATED APPLICATIONS

This application claims the benefit of priority under 35 U.S.C. § 119 to prior filed U.S. Provisional Patent Application No. 63/293,469 filed on Dec. 23, 2021, the entire contents of which is hereby incorporated by reference as if set forth in full herein.

FIELD

The present invention relates generally to medical devices, and in particular, but not exclusively, to catheters with electrodes suitable to ablate cardiac tissues.

BACKGROUND

Cardiac arrhythmias, such as atrial fibrillation (AF), occur when regions of cardiac tissue abnormally conduct electrical signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Medical probes capable of selectively ablating cardiac tissue typically include electrodes disposed on an expandable member positioned at a distal end of a shaft. The shaft is inserted into a lumen of a patient and guided to the heart where the electrodes can be positioned and energized to ablate the cardiac tissue. The expandable member can sometimes include an inflatable balloon and/or spines that are configured to form a predetermined shape when in a deployed state.

Medical probes that utilize an inflatable balloon generally inject saline through the shaft or a catheter to inflate the balloon and to provide irrigation at a location where the cardiac tissue is to be ablated. When the medical procedure is completed, the operator must deflate the balloon so the balloon can be withdrawn through a delivery sheath. The balloon can take some time to deflate due to the saline exiting the inflatable balloon through small irrigation openings. Therefore, there is a need in the art for an apparatus that is capable of draining the expandable member quickly when the expandable member is to be withdrawn through the delivery sheath.

Additionally, current medical probes include handles that are gripped and manipulated by the operator to perform the medical procedure. These handles often include many small parts which can make it difficult to manufacture and assemble the handle. Therefore, there is a need in the art for a handle having fewer components to help reduce the overall cost and complexity of manufacturing and assembling the medical probe. These and other problems can be addressed by the technology disclosed herein.

SUMMARY

There is provided, in accordance with an embodiment of the present invention, a medical probe, including a handle, a shaft, a balloon, and a coupler. The handle can extend from a proximal portion to a distal portion. The shaft can extend from the distal portion of the handle and be coupled to a proximal portion of a balloon disposed at a distal portion of the shaft.

The coupler can be disposed between the shaft and the proximal portion of the balloon. The coupler can include a first portion having a first aperture disposed therethrough and a second portion slidably coupled to the first portion and having a second aperture disposed therethrough. The second portion can be sized to be inserted at least partially into the first portion. The second portion can be configured to slide between a first position and a second position relative the first portion.

The coupler can include a vent port proximate a proximal end of the second portion. The vent port can be configured such that when the second portion is in the first position, the vent port is at least partially obstructed by the first portion, and when the second portion is in the second position, the vent port is unobstructed by the first portion.

The medical probe can include a spring that configured to prevent the second portion from moving to the second position unless a predetermined force is applied to either the first portion or the second portion. The spring can extend between the first portion and the second portion. The medical probe can include a second spring disposed on a side of the coupler that is opposite the first spring.

The medical probe can include a hollow tube disposed along a side of the second portion and the vent port can be disposed in the hollow tube. The hollow tube can extend from approximately a distal portion of the second portion to approximately a distal end of the first portion. The hollow tube can be configured to permit fluid to flow from a balloon of the medical probe when the second portion is in the second position.

The first portion of the coupler can be sized to receive a sheath of the medical probe and the second portion of the coupler can be size to be inserted at least partially into a balloon of the medical probe.

The second portion can include a third aperture sized to receive a wire of an electrode assembly of the medical probe.

The first aperture and the second aperture of the coupler are axially aligned and sized to permit a catheter of the medical probe to pass therethrough.

The second portion of the coupler can further include a raised end that is configured to prevent the second portion from decoupling from the first portion.

The medical probe can include an actuator shaft extending from the shaft to a distal portion of the balloon. The actuator shaft can be configured for movement along a longitudinal axis. The actuator shaft can be coupled to a nose piece at the distal portion of the balloon and the nose piece can be coupled to the distal portion of the balloon. The nose piece can include a cylindrical body that is configured to be coupled to the distal portion of a balloon catheter. The cylindrical body can include an outer diameter of less than 0.14 inches and include an aperture extending therethrough from a proximal end of the cylindrical body to a distal end of the cylindrical body. The aperture can be sized to receive a catheter of the medical probe. In some examples, the outer diameter of the nose piece is approximately 0.11 inches.

The nose piece can include a beveled end piece proximate the distal end of the cylindrical body of the nose piece. The nose piece can include a ridge configured to form an interference fit with a coupler disposed proximate the distal portion of the balloon catheter. The nose piece can include a second aperture extending therethrough from the distal portion of the cylindrical body to the proximal end of the cylindrical body. The second aperture can be configured to permit a fluid to pass therethrough from a balloon of the medical probe and out the distal end of the cylindrical body.

The nose piece can include a shoulder extending inwardly into the aperture and configured to prevent the actuator shaft from passing through the aperture from the proximal end to the distal end. The shoulder can be positioned such that the actuator shaft is permitted to extending at least partially into the aperture.

The medical probe can include a strain relief hub coupled to the handle. The strain relief hub can include a first portion that is configured to be inserted at least partially into the handle of the medical probe. The first portion can include a first aperture extending therethrough and a shoulder configured to interface with the handle of the medical probe to prevent the strain relief hub from sliding proximally or distally along the handle.

The strain relief hub can include a second portion attached to the first portion and having a second aperture extending therethrough. The first aperture and the second aperture can be axially aligned and configured to receive a catheter tube of the medical probe. The second portion can have a smaller inner diameter than an inner diameter of the first portion.

The first portion and the second portion of the strain relief hub can include threaded fittings such that the second portion is threadably attachable to the first portion. The second portion can be configured to reduce an inner diameter of the first portion when the second portion is attached to the first portion such that the catheter tube passing through the first portion is secured in place by the first portion.

The first portion of the strain relief hub can include a recess extending approximately midway through the first portion. The first portion of the strain relief hub can include a second shoulder configured to interface with the handle of the medical probe to prevent the strain relief hub from sliding proximally or distally in the handle.

The second portion of the strain relief hub can include a sloped end proximate a distal end of the second portion.

The disclosed technology can include a handle for a medical probe. The handle can include a handle body extending along a longitudinal axis from a proximal portion to a distal portion. The handle can be configured to permit other components to pass therethrough.

The handle can include a strain relief hub disposed at a distal portion of the handle body. The strain relief hub can include a first portion that is configured to be inserted at least partially into the handle body. The first portion can include a first aperture extending therethrough and a shoulder configured to interface with the handle body to prevent the strain relief hub from sliding proximally or distally in the handle body. The handle can include a second portion attached to the first portion and comprising a second aperture extending therethrough. The first aperture and the second aperture can be axially aligned and configured to receive a catheter of the medical probe.

The second portion of the strain relief hub can be configured to reduce an inner diameter of the first portion when the second portion is attached to the first portion such that the catheter passing through the first portion is secured in place by the first portion.

The first portion of the strain relief hub can include a recess extending approximately midway through the first portion. The first portion of the strain relief hub can include a second shoulder configured to interface with the handle of the medical probe to prevent the strain relief hub from sliding proximally or distally in the handle.

The second portion of the strain relief hub can include a sloped end proximate a distal portion of the second portion.

The disclosed technology can include a method of preparing an expandable member of a medical probe for a medical procedure. The method can include inserting the expandable member into an insertion tool so that the expandable member extends beyond the insertion tool, submerging the expandable member in a fluid, and setting a fluid pump of the medical probe to pump the fluid at a first flow rate through the expandable member.

With the expandable member submerged in the fluid, the method can include setting the fluid pump to pump the fluid at a second flow rate, the second flow rate being less than the first flow rate. The method can include pulling the expandable member into the insertion tool with the expandable member and insertion tool being submerged.

The method can include inserting the insertion tool with the expandable member disposed inside the insertion tool partially into a sheath valve, pushing the expandable member through a delivery sheath until the expandable member is extended outside a distal portion of the delivery sheath, setting the fluid pump to pump fluid at the first flow rate, and applying ablation energy to electrodes disposed on the expandable member.

The first flow rate comprises approximately 35 milliliters per minute and the second flow rate comprises approximately 5 milliliters per minute.

In response to determining that cardiac tissue has been sufficiently ablated by the ablation energy, the method can include setting the fluid pump to pump the fluid at the second flow rate and withdrawing the expandable member back to the delivery sheath.

The method can include moving the expandable member to a new location within a heart, pushing the expandable member through the delivery sheath until the expandable member is extended outside the distal portion of the delivery sheath, setting the fluid pump to pump fluid at the first flow rate, and ablating cardiac tissue proximate the new location with the medical probe. The method can include withdrawing the expandable member entirely from the sheath.

Additional features, functionalities, and applications of the disclosed technology are discussed herein in more detail.

BRIEF DESCRIPTION OF THE DRAWINGS

FIGS. 12A-12B show a flowchart illustrating a method of preparing an expandable member for a medical procedure as well as using the expandable member to perform the medical procedure, in accordance with the disclosed technology.

DETAILED DESCRIPTION

Figure 1:
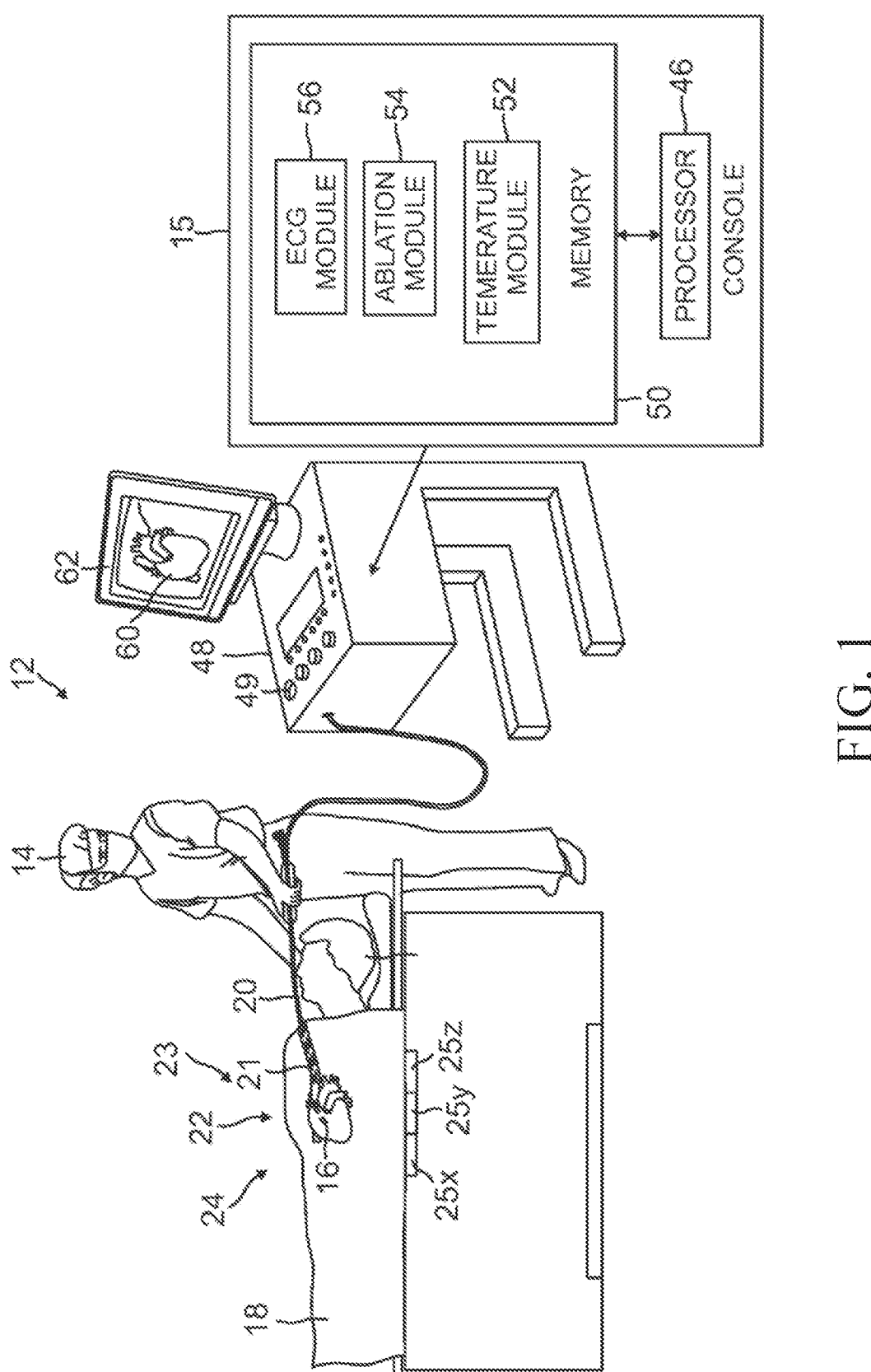
FIG. 1 is a schematic pictorial illustration of a medical procedure using a medical probe, in accordance with the disclosed technology.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%.

As discussed herein, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" or "professional" can include a doctor, surgeon, technician, scientist, or any other individual or delivery instrumentation associated with delivery of a multi-electrode catheter for the treatment of drug refractory atrial fibrillation to a subject. As well, the term "proximal" indicates a location closer to the operator or physician whereas "distal" indicates a location further away to the operator or physician.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface or inner surface without departing from the scope of the present disclosure.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), sometimes referred interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

The present disclosure is related to systems, method or uses and devices which utilize end effectors having electrodes affixed to expandable members such as balloons or spines. Example systems, methods, and devices of the present disclosure may be particularly suited for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures (e.g., expandable members such as a balloon or spines) at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore cryoablation is not viable in certain anatomical geometries which may be reached by electrical ablation devices.

IRE is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by apoptosis. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

Turning now to the figures in which like reference numbers represent like elements, FIG. 1 depicts example instrumentations that include an apparatus 12, according to an example of the present disclosure. The procedure is performed by an operator 14 and is assumed to comprise ablation of a portion of a myocardium 16 of the heart of a human patient 18. However, it is understood that embodiments disclosed herein are not merely applicable to this specific procedure and can include substantially any procedure on biological tissue or on non-biological materials.

To perform the ablation, the operator 14 inserts a probe 20 into a delivery sheath 21 that has been pre-positioned in a lumen of the patient. Delivery sheath 21 is positioned so that a distal end 22 of probe 20 enters the heart of the patient. A multi-electrode radiofrequency balloon catheter 24 (e.g., a balloon catheter) is deployed through a lumen 23 of the probe 20 and exits from a distal end of the probe 20. Catheter 24 can be a multi-electrode radiofrequency balloon catheter for cardiac electrophysiological ablation of pulmonary veins of the atria and, when used with a multi-channel RF generator, for the treatment of drug refractory recurrent symptomatic paroxysmal atrial fibrillation (PAF), as discussed more particularly below. The catheter 24 can be introduced through the femoral artery, wrist artery (radial access) or directly through the carotid artery. While both radial and carotid access avoids the aortic arches, there are other drawbacks. However, all three approaches are considered to be known to ones of skill in this art.

Functionally, catheter 24 seeks to achieve isolation of the pulmonary veins in the subject's left atrium (LA) to eliminate symptoms of AF. The catheter 24 ablates from multiple irrigated, independently-controlled electrodes simultaneously. The amount of power delivered to each electrode is controlled independently to improve safety and lesion quality.

One RF generator contemplated for use in this disclosure can be for cardiac ablation applications to generate RF energy for delivery to a site in the heart via compatible RF ablation catheters. The generator is capable of independently controlling the delivery of RF energy to electrodes simultaneously. The generator can include functions for controlling ablation parameters at the ablation electrodes of the catheter. Ablation parameters, such as power, impedance, ablation duration, and temperature are recorded and can be exported at the end of the procedure to a portable memory device, cloud storage, or other storage.

As shown in FIG. 1, apparatus 12 is controlled by a system processor 46, which is in an operating console 15 of the apparatus. Console 15 comprises controls 49 which are used by operator 14 to communicate with the processor 46. The console 15 can be housed in a control station 48 and be configured to output data 60 to a display 62 such that the operator 14 is able to view information about the procedure.

During the procedure, the processor 46 typically tracks a location and an orientation of the distal end 22 of the probe 20, using any method or use known in the art. For example, processor 46 can use a magnetic tracking method or use, wherein magnetic transmitters 25X, 25Y and 25Z external to the patient 18 generate signals in coils positioned in the distal end of the probe 20. The CARTO® system (available from Biosense Webster, Inc. of Irvine, California) uses such a tracking method or use.

To operate apparatus 12, the processor 46 communicates with a memory 50, which has many modules used by the processor 46 to operate the apparatus. Thus, the memory 50 comprises a temperature module 52, an ablation module 54, and an electrocardiograph (ECG) module 56. The memory 50 typically comprises other modules, such as a force module for measuring the force on the distal end 22, a tracking module for operating the tracking method or use used by the processor 46, and an irrigation module allowing the processor to control irrigation provided for the distal end 22.

While other modules are not illustrated in FIG. 1, others are indeed contemplated and can include hardware as well as software elements. For example, module 54 can include a radio-frequency generator with at least one output or output channel, e.g., ten outputs or ten output channels. Each of the outputs can be separately and selectively activated or deactivated by a switch. That is, each switch can be disposed between the signal generator and a respective output. Thus, a generator with ten outputs would include ten switches. These outputs can each be individually coupled to electrodes on an ablation catheter, e.g., the ten electrodes 33 on balloon 80, described in further detail below. Electrodes 33 can be irrigated, flexible gold-plated electrodes bonded thereto and used to deliver RF energy in a unipolar fashion to the tissue and sense temperature at each electrode. Electrodes 33 can be oriented circularly to achieve good circumferential contact with the ostia of the pulmonary veins. The catheter 24 can ablate cardiac tissue from the independently-controlled electrodes simultaneously when paired with a Multi-Channel RF generator and the amount of power delivered to each electrode is controlled independently.

Such an electrical connection can be achieved by establishing an electrical path between each output and each electrode. For example, each output can be connected to a corresponding electrode by one or more wires or suitable electrical connectors. Thus, in some embodiments, an electrical path can include at least one wire. In some embodiments, the electrical path can further include an electrical connector and at least a second wire. Thus, electrodes 33 can be selectively activated and deactivated with the switches to receive radiofrequency energy separately from each of the other electrodes.

Figure 2:
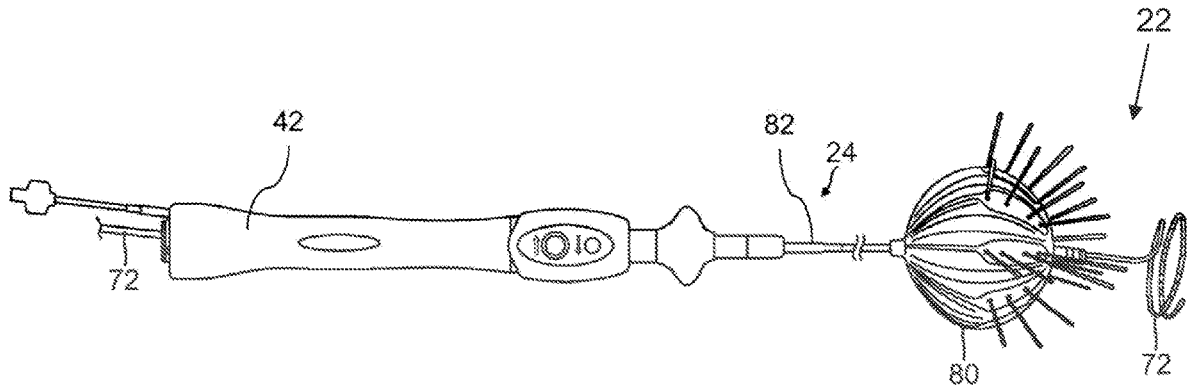
FIG. 2 is a schematic pictorial illustration of a top view of an example medical probe with a balloon in an expanded state, in use with a lasso catheter.

FIG. 2 is a top view of catheter 24. Catheter 24 has a usable length of approximately 110 cm (though other dimensions are contemplated as needed or required). Catheter 24 can have three major sections: handle 42, shaft 82 and distal end 22. The shaft 82 can measure 10.5 F with a 13.5 F maximum outer diameter around the balloon 80 when the balloon 80 is in its fully collapsed state. The catheter 24 can have a high-torque shaft 82, with a unidirectional braided deflectable tip section. The shaft allows the plane of the curved tip with balloon 80 to be rotated to facilitate accurate positioning of the catheter tip to the desired site (ostia of the pulmonary veins). The compliance of the balloon 80 allows for its flexible surface electrodes 33 to conform to the anatomy when pressed against the tissue.

The handle 42 can incorporate a deflection thumb knob allowing for unidirectional deflection, a balloon advancement mechanism, and a luer fitting for balloon inflation and irrigation. An additional luer fitting can be included and located proximally to the ejector and serve as an entry port for a guidewire as well as distal irrigation and/or contrast injection. The catheter 24 can be used with an irrigation pump to control irrigation to the balloon. Heparinized normal saline can be delivered through the luer fitting of the handle 42.

The catheter 24 is shown in FIG. 2 having a lasso catheter 72 at a distal end of the balloon 80, however, other catheters can be inserted through the balloon 80 such as a guide wire, a diagnostic catheter, or any other suitable catheter for the application. In other words, the balloon 80 can include a lumen passing therethrough to permit a catheter to pass through the balloon 80.

Figure 3A:
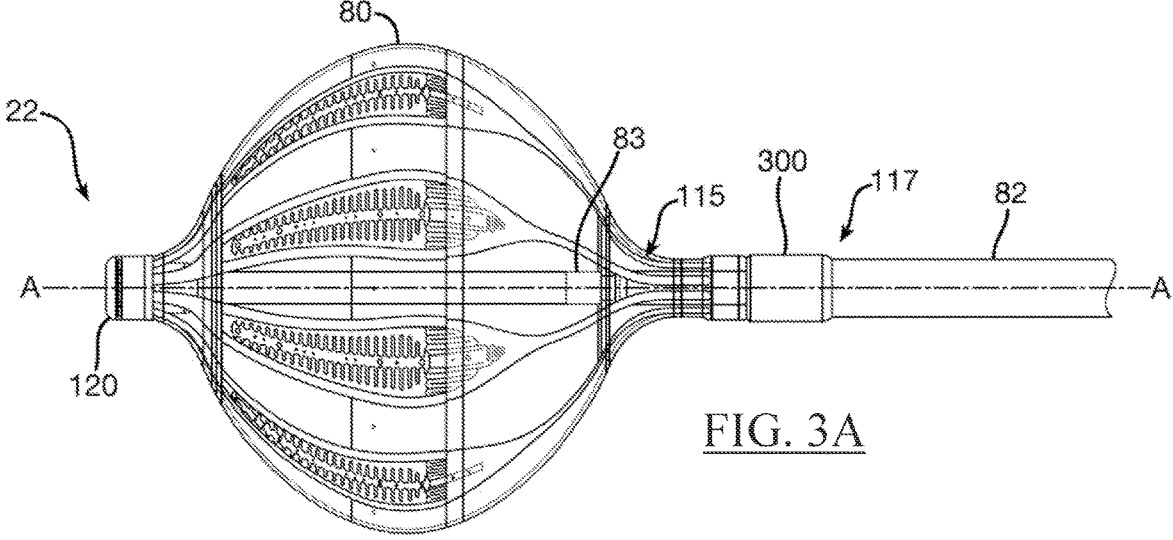
FIG. 3A is a schematic pictorial illustration of a side view of the balloon and a shaft attached to a coupler, in accordance with the disclosed technology.
Figure 3B:
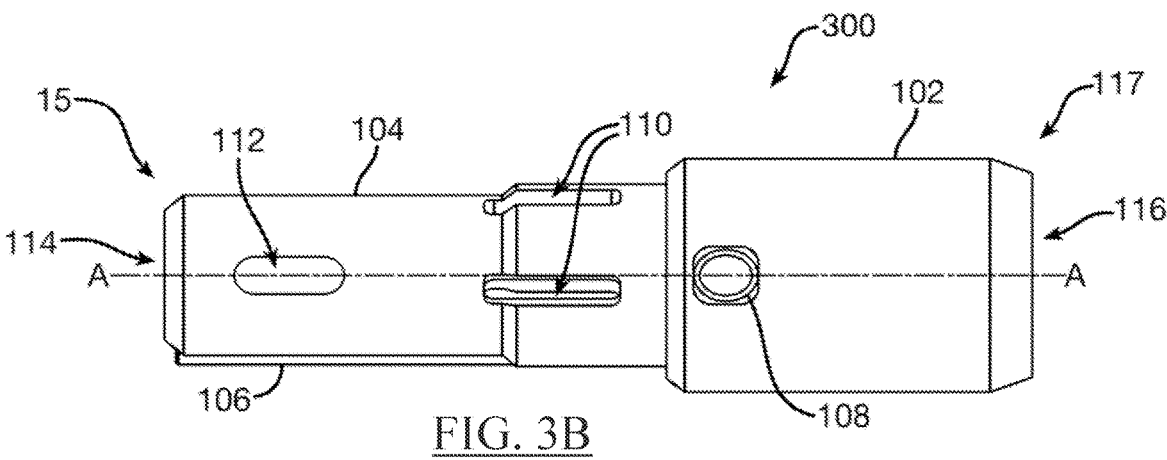
FIG. 3B is a schematic pictorial illustration of a side view of a coupler, in accordance with the disclosed technology.
Figure 4A:
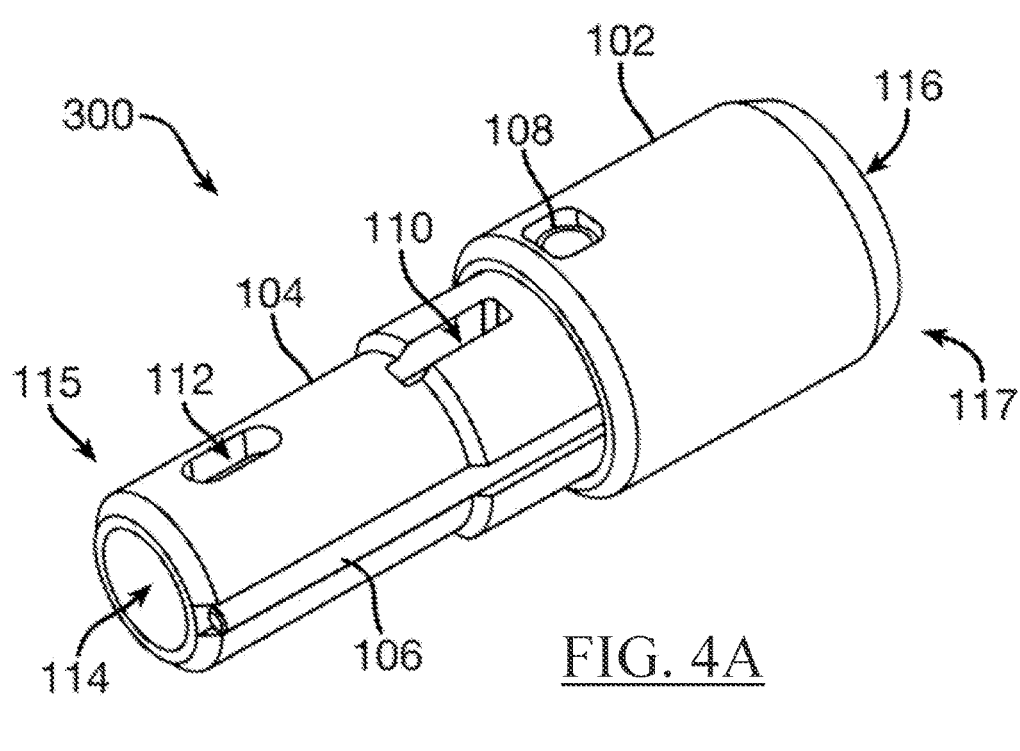
FIG. 4A is a schematic pictorial illustration of a perspective view of a coupler, in accordance with the disclosed technology.
Figure 4B:
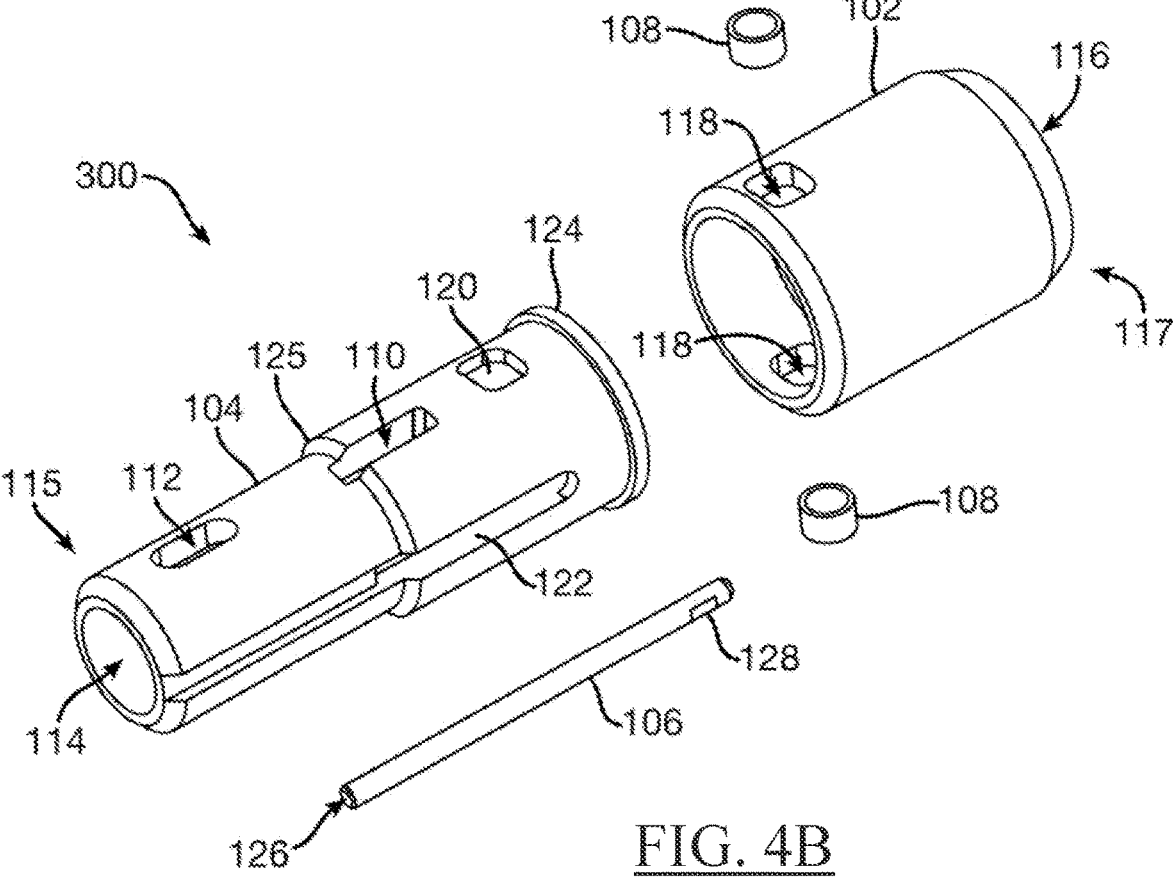
FIG. 4B is a schematic pictorial illustration of an exploded perspective view of a coupler, in accordance with the disclosed technology.

FIG. 3A is a schematic pictorial illustration of a side view of the balloon 80 and a shaft 82 both attached to a coupler 300, in accordance with the disclosed technology. The shaft 82 can be a catheter tube that is configured to guide the balloon 80 through the delivery sheath 21 to the patient's 18 heart. The balloon 80 and the shaft 82 can be attached to coupler 300 with the balloon being attached to the distal end 115 of the coupler 300 and the shaft being attached to the proximal end 117 of the coupler 300. The coupler 300 can be sized to fit through the delivery sheath 21.

An actuator shaft 83 is shown inside of the balloon 80 and extending along a longitudinal axis (A-A) of the balloon 80. The actuator shaft 83 can extend from the shaft 82 through the balloon 80 and be attached to a distal end 22 of the balloon 80. The actuator shaft 83 can be configured to slide or otherwise move along the longitudinal axis of the balloon 80 such that the actuator shaft 83 can facilitate expansion, retraction, and manipulation the balloon 80 to perform the medical procedure. The actuator shaft 83 can, in some examples, include an aperture therethrough to permit a guidewire, irrigation fluid, a catheter, or other components or elements to pass therethrough to be delivered near the distal end 22 of the balloon 80.

Figure 5A:
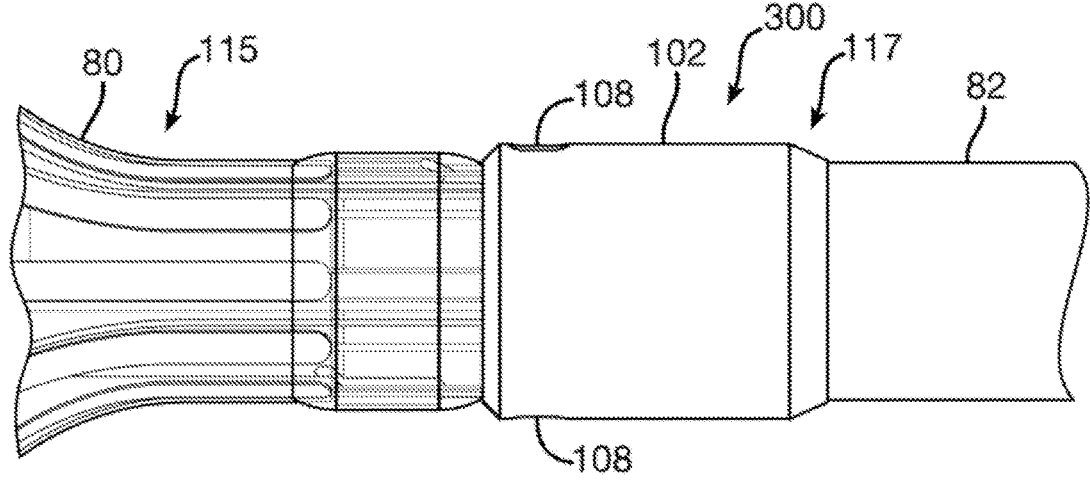
FIG. 5A is a schematic pictorial illustration of a side view of a balloon and a shaft attached to a coupler in a first position, in accordance with the disclosed technology.
Figure 5B:
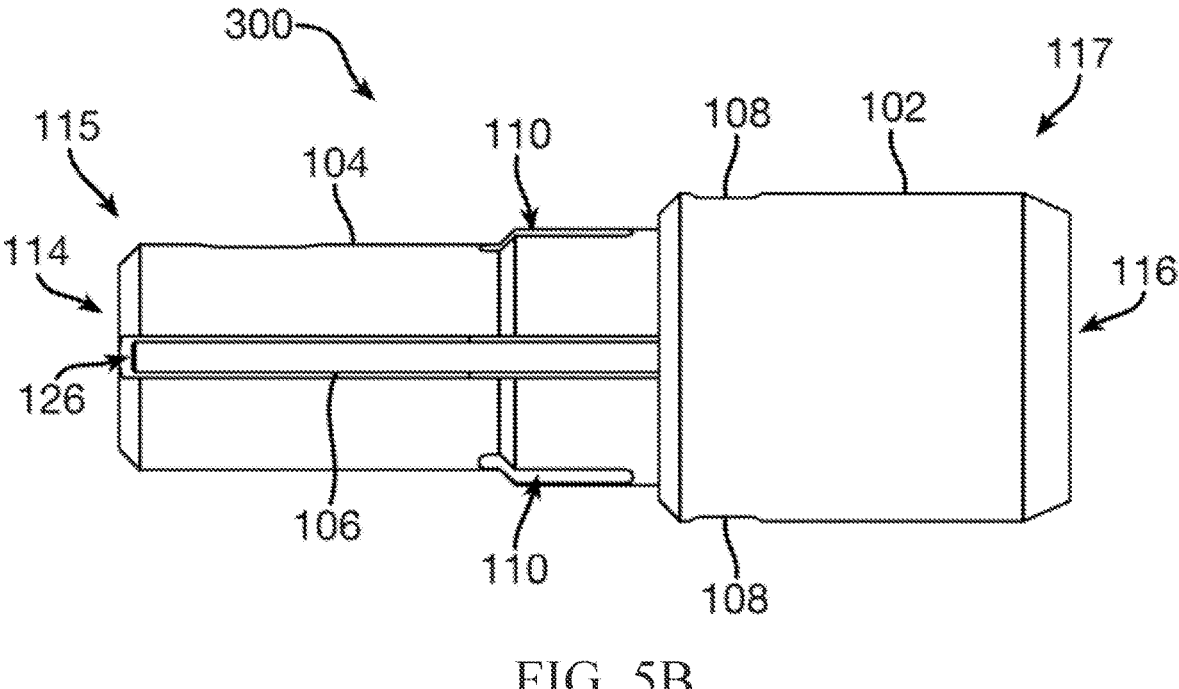
FIG. 5B is a schematic pictorial illustration of a side view of the coupler in a first position, in accordance with the disclosed technology.
Figure 6A:
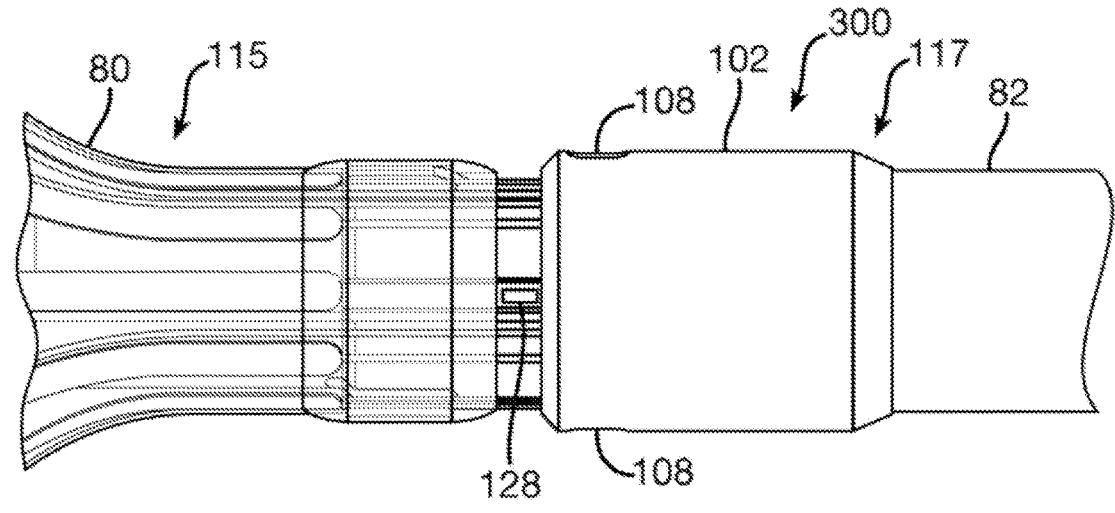
FIG. 6A is a schematic pictorial illustration of a side view of a balloon and a shaft attached to a coupler in a second position, in accordance with the disclosed technology.
Figure 6B:
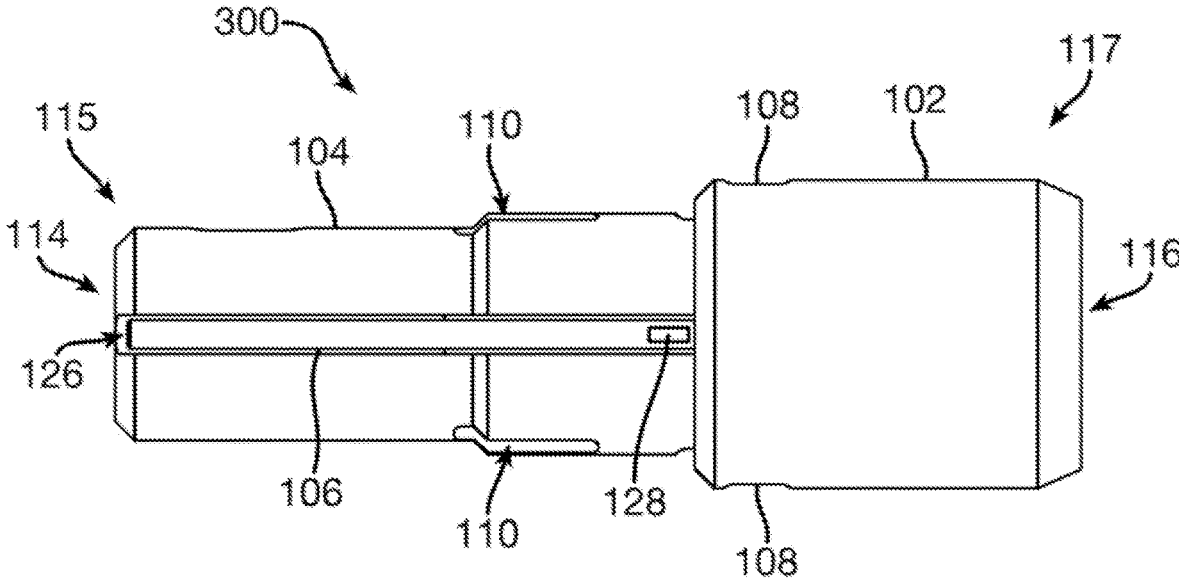
FIG. 6B is a schematic pictorial illustration of a side view of the coupler in a second position, in accordance with the disclosed technology.

As illustrated in FIGS. 3B-4B, the coupler 300 can include a first portion 102 and a second portion 104 slidably attached to the first portion 102. The second portion 104 can slide along the longitudinal axis (A-A) relative to the first portion 102 between a first position (as illustrated in FIGS. 5A-5B) and a second position (as illustrated in FIGS. 6A-6B). In the first position, the coupler 300 can be configured to prevent fluid from draining from the balloon 80 and in the second position, the coupler 300 can be configured to permit fluid to drain from the balloon 80. In this way, the coupler 300 can be configured to facilitate quickly draining fluid from the balloon 80 such that the balloon 80 can be withdrawn through the delivery sheath 21.

The first portion 102 can include an aperture 116 extending therethrough along the longitudinal axis and the second portion 104 can similarly include an aperture 114 extending therethrough along the longitudinal axis. The aperture 116 of the first portion 102 and the aperture 114 of the second portion 104 can each be sized to permit electrical wires, a guide wire, the actuator shaft 83, a catheter tube, and/or other components or elements to pass therethrough.

The coupler 300 can include a vent port 128 that can be configured to permit saline or other fluid to drain from the balloon 80 when the second portion 104 is in the second position (as illustrated in FIGS. 6A-6B). When the second portion 104 is in the first position, however, the vent port 128 can be at least partially obstructed by the first portion 102 such that the coupler 300 can prevent saline or other fluid from draining from the balloon 80 through the vent port 128 (as illustrated in FIGS. 5A-5B). The coupler 300 can be configured such that the second portion 104 remains in the first position and fluid is prevented from draining through the vent port 128 until a sufficient force is applied to the first portion 102 and/or the second portion 104. For example, the first portion 102 and the second portion 104 can be caused to remain in the first position until one or both are pulled in opposite directions to cause the second portion 104 to move to the second position and uncover the vent port 128. To illustrate, when the balloon 80 is pulled back into the delivery sheath 21, the force of the balloon 80 contacting the edges of the delivery sheath 21 can cause the second portion 104 to be moved to its second position such that the vent port 128 is unobstructed by the first portion 102. In this way, the vent port 128 can allow the fluid to drain from the balloon 80 to enable the operator 14 to withdraw the balloon 80 back through the delivery sheath 21.

To help ensure the second portion 104 remains in the first position and the vent port 128 is at least partially obstructed by the first portion 102, the coupler 300 can include one or more springs 108 that are configured to retain the first portion 102 and the second portion 104 in the first position. For example, the coupler 300 can include springs 108 disposed on opposite sides of the coupler 300. The springs 108 can extend between the first portion 102 and the second portion 104 and be configured such that the spring applies a force to the first portion 102 and the second portion 104 to cause the second portion 104 to remain in the first position. The first portion 102 can include a spring aperture 118 and the second portion can include a spring recess 120. The spring aperture 118 and the spring recess 120 can be configured to receive the spring 108 and prevent the spring 108 from becoming dislodged from the coupler 300. The spring 108 can be sized and configured such that the spring force is sufficient to retain the second portion 104 in the first position until a sufficient force is applied to the first portion 102, the second portion 104, or both to cause the second portion 104 to move to the second position.

Although the springs 108 are illustrated as being separate from the first portion 102 and the second portion 104, the springs 108 can be integrated into the first portion 102 or the second portion 104. For example, the spring 108 can be formed into a side of the first portion 102 or the second portion 104 as a compliant mechanism to cause the second portion 104 to remain in the first position until a sufficient force is applied.

The second portion 104 can include one or more component apertures 110 that can be formed into a side of the second portion 104 to permit a wire or other component to pass therethrough. For example, the component apertures 110 can be sized such that a wire can pass therethrough to connect to an electrode. The second portion 104 can further include a fluid aperture 112 to permit fluid (e.g., irrigation fluid such as saline) to pass therethrough to facilitate inflation of the balloon 80 and irrigation proximate the electrodes.

The second portion 104 can include a raised end 124 that can be configured to contact an inner surface of the first portion 102 such that the second portion 104 is prevented from being decoupled from the first portion 102. In other words, the raised end 124 can be configured to prevent the second portion 104 from passing entirely through the first portion 102 when a force is applied to the second portion 104 pulling the second portion 104 away from the first portion 102.

The second portion 104 can include a raised shoulder 125 that can be sized for attachment to the balloon 80. For example, the balloon 80 can be attached to the second portion 104 between the raised shoulder 125 and the raised end 124. In this way, the second portion 104 can have a distal end 115 that is a smaller outer diameter than the raised shoulder 125 to facilitate easier removal of the balloon 80 through the delivery sheath 21.

The second portion 104 can include a channel 122 formed into a side of the second portion 104 and sized to receive a hollow tube 106. The hollow tube 106 can have a lumen 126 extending at least partially therethrough and the vent port 128 can be formed into the hollow tube 106. In this way, fluid inside of the balloon 80 can pass through the hollow tube 106 and drain out the vent port 128 when the vent port 128 is unobstructed. The channel 122 can be sized such that the hollow tube 106 can fit between the second portion 104 and the first portion 102 when the second portion 104 is in the first position. Although the hollow tube 106 is illustrated as terminating proximate the distal end 115 of the coupler 300, the hollow tube 106 can extend beyond the distal end 115 of the coupler 300 or terminate before reaching the distal end 115 of the coupler 300 as would be suitable for the particular application.

FIG. 5A illustrates the coupler 300 in the first position with the balloon 80 and the shaft 82 attached to the coupler while FIG. 5B illustrates only the coupler 300 in the first position. As shown, when the second portion 104 is in the first position, the first portion 102 can obstruct the vent port 128 such that fluid inside of the balloon 80 is prevented from draining through the vent port 128.

FIG. 6A illustrates the coupler 300 in the second position with the balloon 80 and the shaft 82 attached to the coupler while FIG. 6B illustrates only the coupler 300 in the second position. As shown, when the second portion 104 is in the second position, the first portion 102 does not obstruct the vent port 128 and, therefore, fluid inside of the balloon 80 is permitted to drain through the vent port 128. In this way, the coupler 300 can facilitate drainage of fluid from the balloon 80 when the balloon 80 is pulled back into the delivery sheath 21 or is otherwise no longer necessary to remain inflated.

Figure 7A:
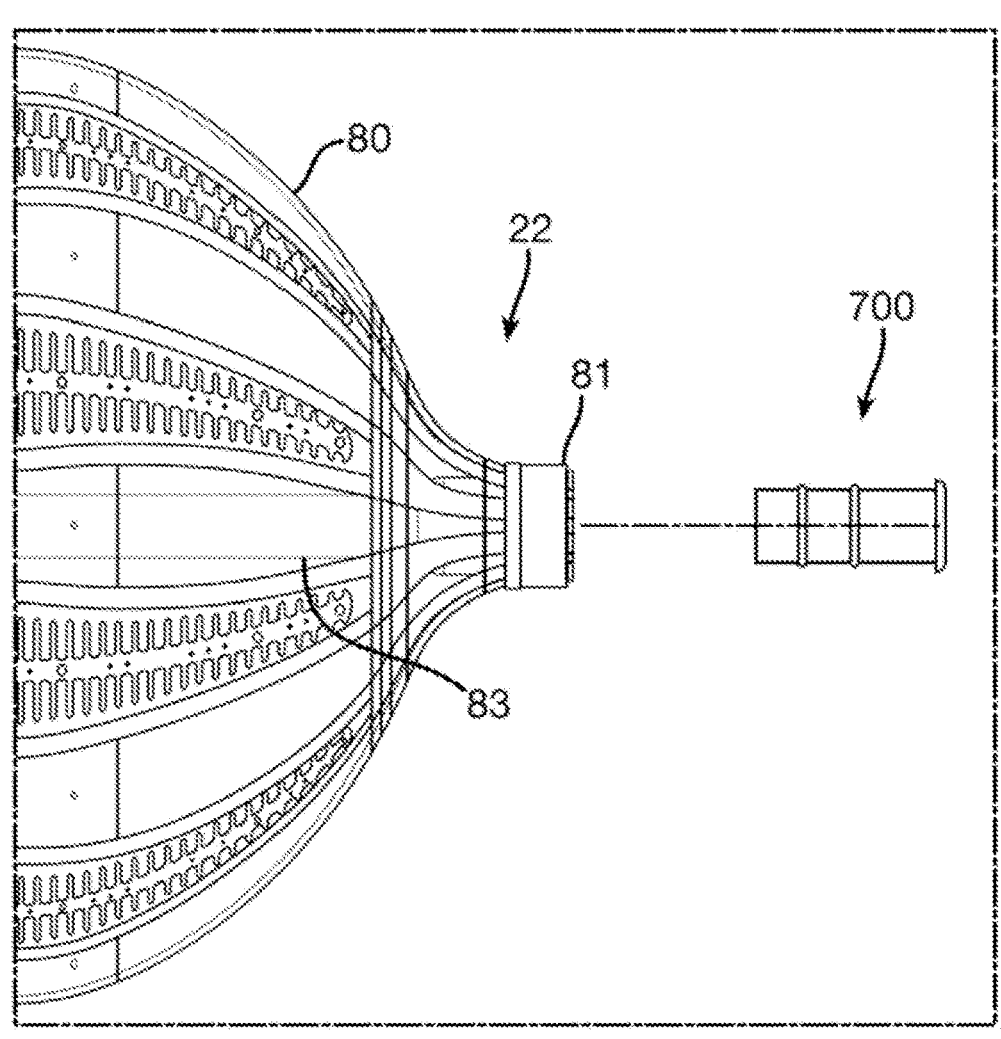
FIG. 7A is a schematic pictorial illustration of a side view of the balloon and a nose piece, in accordance with the disclosed technology.
Figure 7B:
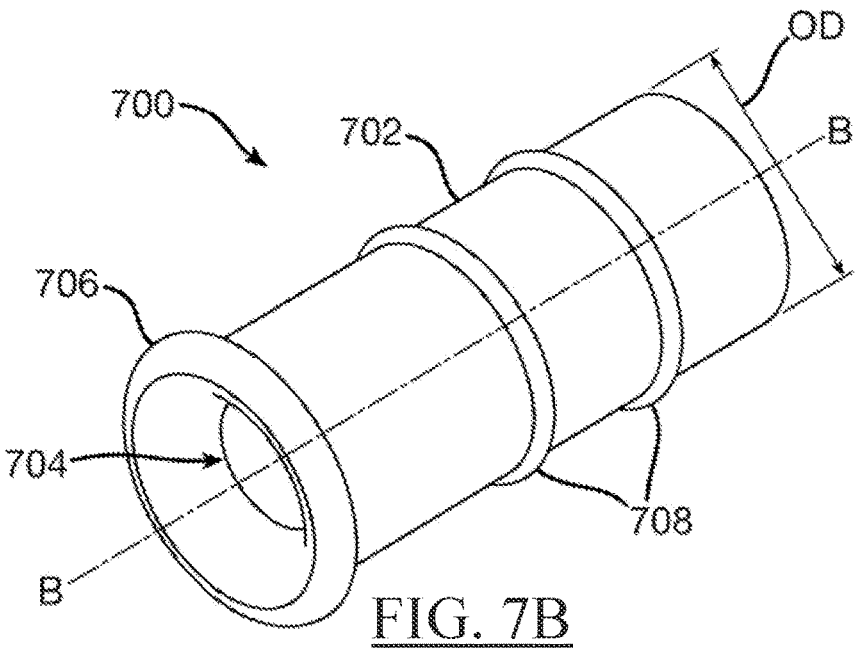
FIG. 7B is a schematic pictorial illustration of a perspective view of a nose piece, in accordance with the disclosed technology.

FIG. 7A is a schematic pictorial illustration of a side view of the balloon 80 and a nose piece 700 while FIG. 7B is a schematic pictorial illustration of a perspective view of the nose piece 700, in accordance with the disclosed technology. The nose piece 700 can be coupled to the distal end 22 of the balloon 80 and, in some examples, can be attached to the actuator shaft 83. The nose piece 700 can have a cylindrical body 702 and an aperture 704 extending therethrough from a proximal end of the nose piece 700 to a distal end of the nose piece 700. The aperture 704 can be sized to permit a catheter, a guide wire, or other component to pass therethrough.

The nose piece 700 can have an outer diameter than is less than 0.14 inches to ensure the balloon 80 and the nose piece 700 are able to fit within the delivery sheath 21. In some examples, the outer diameter of the nose piece 700 can be approximately 0.11 inches.

The nose piece 700 can include one or more ridges 708 that can be sized and positioned to form an interference fit with a nose coupler 81 positioned at the distal end 22 of the balloon 80. The nose coupler 81 and the nose piece 700 can, together, secure the balloon 80 and the actuator shaft 83 in place such that the balloon 80 can be inflated, deflated, and manipulated as necessary.

The nose piece 700 can include a beveled end piece 706 that can have an outer diameter that is larger than the outer diameter of the cylindrical body 702 but is still able to fit within the delivery sheath 21. The beveled end piece 706 can be sloped such that sharp edges are reduced at the distal end of the nose piece 700 to help reduce the likelihood that components passing through the nose piece 700 could become damaged by a sharp edge.

Figure 8A:
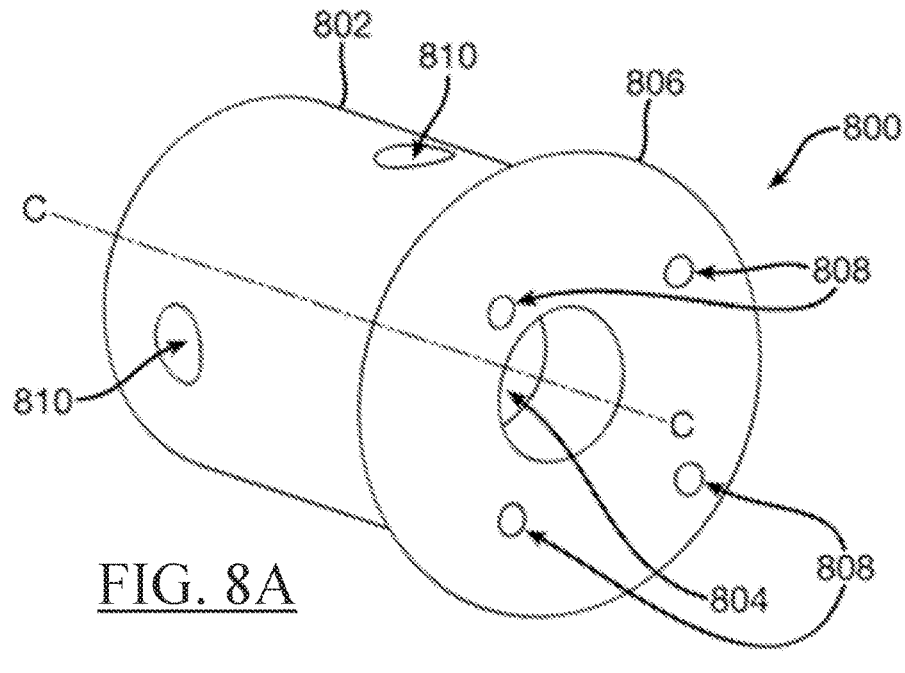
FIG. 8A is a schematic pictorial illustration of a perspective view of a nose piece, in accordance with the disclosed technology.

FIG. 8A is a schematic pictorial illustration of a perspective view of a nose piece 800, in accordance with the disclosed technology. Similar to the nose piece 700, the nose piece 800 can include a cylindrical body 802, an aperture extending therethrough, and a beveled end piece 806. The nose piece 800 can further include drainage apertures 808 extending through the nose piece 800 from the proximal end to the distal end. The drainage apertures 808 can be configured to permit fluid (e.g., saline or other irrigation fluid) to drain from the balloon 80 and/or to provide irrigation at the distal end 22 of the balloon 80. In some examples, the nose piece 800 can include four drainage apertures 808 equally spaced from each other.

The nose piece 800 can further include side apertures 810 that can extend from a side of the cylindrical body 802 and to the aperture 804 extending through the nose piece 800. The side apertures 810 can be configured to permit fluid to flow between the aperture 804 and the outside of the cylindrical body 802 within the balloon 80 to help alleviate pressure that can develop from fluid passing through the nose piece 800.

Figure 8B:
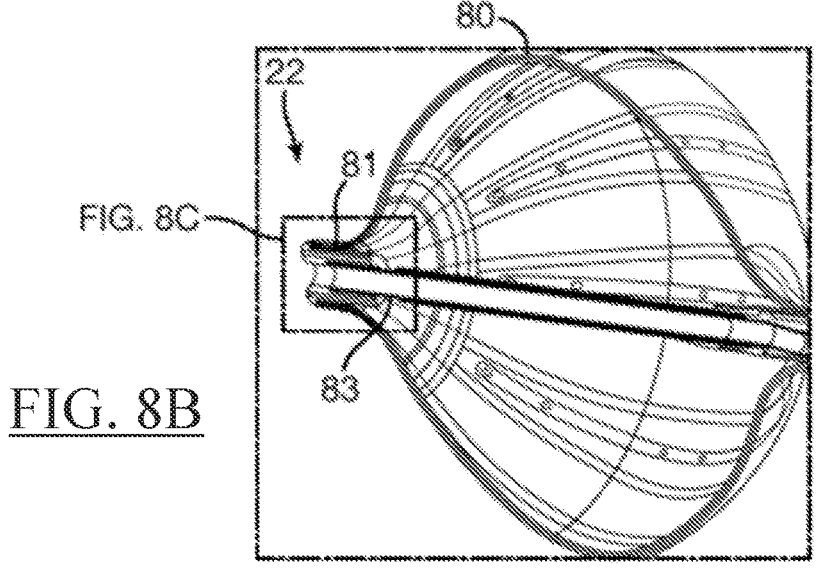
FIG. 8B is a schematic pictorial illustration of a cross-sectional perspective view of a nose piece attached to a balloon.
Figure 8C:
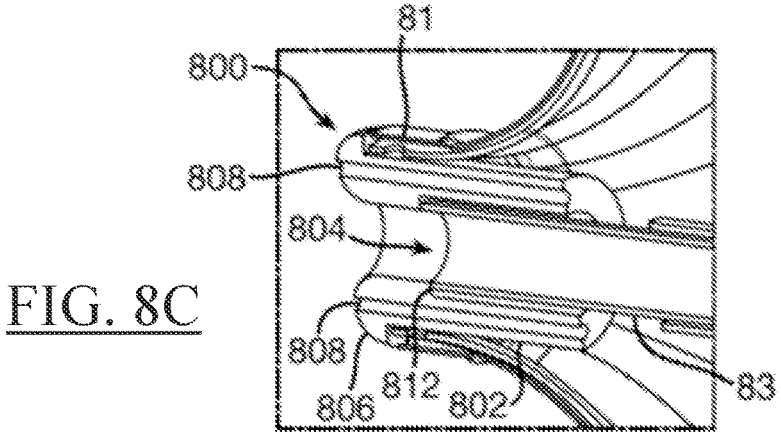
FIG. 8C is a detail view of the nose piece attached to the balloon, in accordance with the disclosed technology.

FIG. 8B is a schematic pictorial illustration of a cross-sectional perspective view of a nose piece 800 attached to the balloon 80 while FIG. 8C is a detail view of the nose piece attached to the balloon 80, in accordance with the disclosed technology. As best illustrated in FIG. 8C, the nose piece 800 can be attached to the distal end of the balloon 80 by an interference fit formed between the nose piece 800 and the nose coupler 81. The balloon 80 can be positioned between the nose piece 800 and the nose coupler 81 such that the balloon 80 is secured to the nose piece 800 and the nose coupler 81.

As illustrated in FIG. 8C, the nose piece 800 can include a shoulder 812 extending inwardly into the aperture 804. The shoulder 812 can be sized and configured to prevent the actuator shaft 83 from passing entirely through the nose piece 800. In other words, the shoulder 812 can be configured to help ensure the actuator shaft 83 is able to push the nose piece 800 and help facilitate inflation, deflation, and manipulation of the balloon 80. The shoulder 812 can be positioned such that the actuator shaft 83 is able to extend at least partially into the nose piece 800.

Figure 9A:
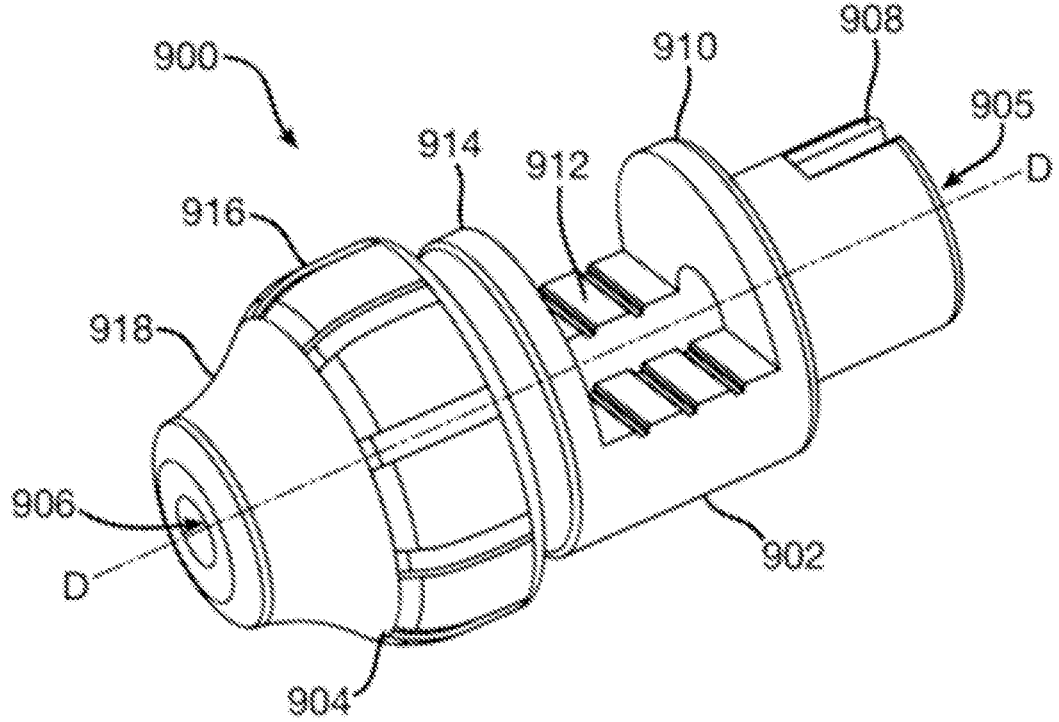
FIG. 9A is a schematic pictorial illustration of a perspective view of a strain relief hub, in accordance with the disclosed technology.
Figure 9B:
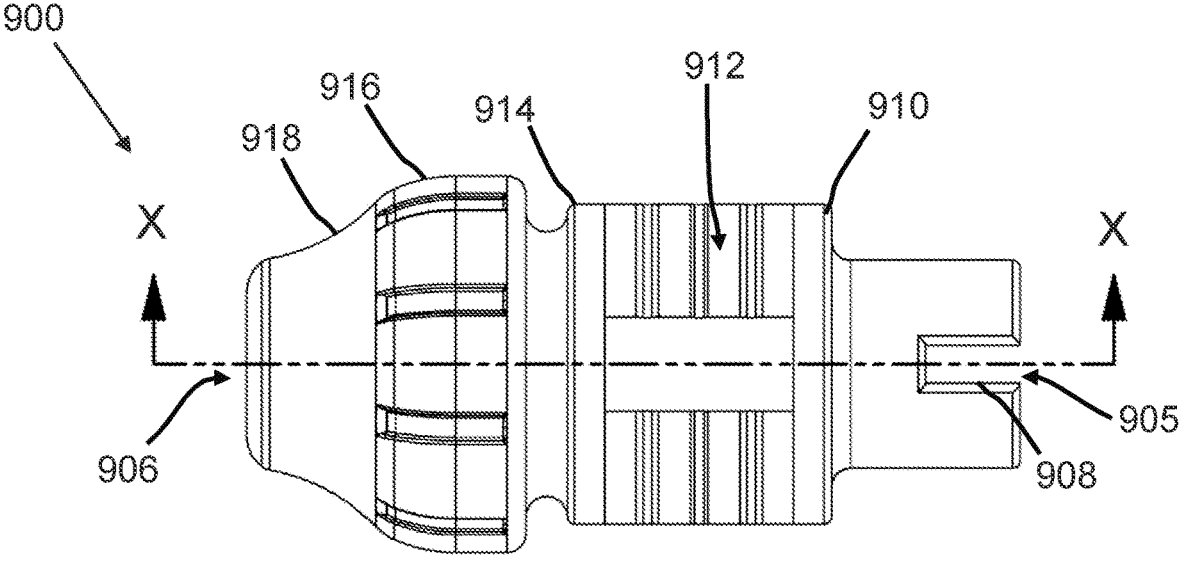
FIG. 9B is a top view of the strain relief hub of FIG. 9A, in accordance with the disclosed technology.
Figure 9C:
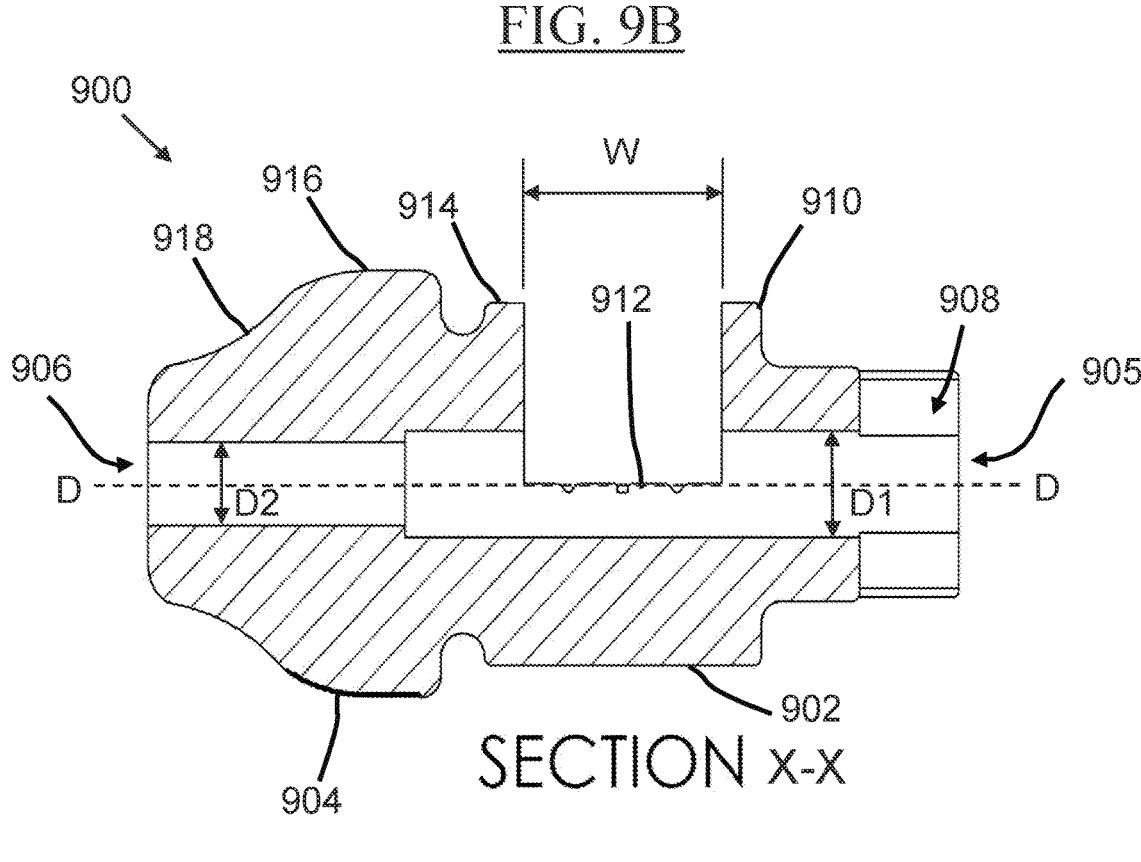
FIG. 9C is a sectional view of the strain relief hub of FIG. 9A and FIG. 9B taken along section line X-X of FIG. 9B, in accordance with the disclosed technology.
Figure 10:
FIG. 10 is a schematic pictorial illustration of a perspective view of a strain relief hub attached to a handle of the medical probe, in accordance with the disclosed technology.

FIGS. 9A-9C illustrate a strain relief hub 900 while FIG. 10 illustrates the strain relief hub 900 assembled with a handle 42, in accordance with the disclosed technology. The strain relief hub 900 can be configured to be coupled to the handle 42 of the medical probe. The strain relief hub 900 can be sized and configured to replace several components that are currently installed in the handle 42 to help reduce the complexity of the handle 42 and to facilitate simple assembly of the handle 42.

The strain relief hub 900 can include a first portion 902 that can be inserted into the handle 42 and a second portion 904 attached to the first portion 902 and extending outwardly from the handle 42. The first portion 902 and the second portion 904 can each include an aperture 905, 906 extending therethrough to permit a catheter, wires, or other components to extend through the strain relief hub 900 and extend outwardly from the handle 42.

The first portion 902 can include a slotted end 908 that can be positioned at a proximate end of the strain relief hub. The slotted end 908 can make it easier for wires and/or a catheter to pass through the strain relief hub 900. The slotted end 908 allows for an upper handle cover half (not shown in FIG. 10 for clarity) to engage with slotted end 908 and retain the handle cover upper half to the strain relief hub 900 and the lower handle cover half 45. The slotted end 908 can engage with a protrusion extending from the handle cover upper half and/or the handle cover lower half 45 to help keep the strain relief hub 900 in place when the handle 42 and the strain relief hub 900 are fully assembled together.

The first portion 902 can further include a first shoulder 910 that can be configured to interface with the handle 42 to prevent the strain relief hub 900 from sliding proximally along the handle 42. The strain relief hub 900 can further include a second shoulder 914 that can be configured to interface with the handle 42 to prevent the strain relief hub 900 from sliding distally along the handle 42. In other words, the first shoulder 910 and the second shoulder 914 can be configured to secure the strain relief hub 900 in place and prevent the strain relief hub 900 from sliding proximally or distally along the handle 42 when the strain relief hub 900 is installed in the handle 42.

FIG. 10 illustrates the strain relief hub 900 assembled with the handle 42. The handle 42 is shown as partially disassembled so that the internal components of the handle 42 are visible. As illustrated in FIG. 10, the handle 42 can include an end ridge 43 configured to contact the second shoulder 914 and a protrusion 44 configured to contact the first shoulder 910 when the strain relief hub 900 is installed in the handle 42 to prevent the strain relief hub 900 from sliding proximally or distally within the handle 42. In other words, the strain relief hub 900 can be sized. such that the first shoulder 910 contacts (or nearly contacts) the protrusion 44 while the second should 914 contacts (or nearly contacts) the end ridge 43 such that the strain relief hub 900 is preventing from sliding proximally or distally within the handle 42 when assembled with the handle 42.

FIG. 9B is a top view of the strain relief hub 900 while FIG. 9C is a sectional view of the strain relief hub 900 taken along section line X-X of FIG. 9B. As illustrated in FIG. 9C, the aperture 905 through the first portion 902 can have a larger inner diameter (D2) than the inner diameter (D1) of the aperture 906 through the second portion 904. In this way, the wires and/or catheters passing through the second portion 904 can be better secured in place.

As illustrated in FIG. 9C, the strain relief hub 900 can further include a recess 912 that can extend approximately midway through the first portion 902. The recess 912 can have a width (W) extending between the first shoulder 910 and the second shoulder 914 as measured along the longitudinal axis D-D. The width (W) can be sized to facilitate assembly of the strain relief hub 900 with wires and/or catheters. The recess 912 can expose the wires and/or catheter extending through the strain relief hub 900 to make it easier to assemble the handle 42 and its components. For example, the recess 912 can be used to facilitate applying adhesive to the wires and/or catheters to ensure a proper bond together and with the strain relief hub 900 to ensure the wires and/or catheters are properly secured. The recess 912 can further include ridges or a rough surface to facilitate better adhesion. Furthermore, because the recess 912 extends approximately midway through the strain relief hub 900 to expose the wires and/or catheter, ultraviolet (UV) light or other curing techniques processes can be used to accelerate the cure time of adhesives used to bond the wires and/or catheters to the strain relief hub 900. Furthermore, the recess 912 can enable inspection of the wires and/or catheters to ensure proper positioning and adhesion once assembled. As well, recess 912 can reduce the overall material used to manufacture the strain relief hub 900, reducing the overall weight of the handle 42 when fully assembled.

In one exemplary embodiment, the strain relief hub 900 is an integrated unitary member where both portions 902 and 904 are formed as a one-piece member shown in the sectional view of FIG. 9C. In other words, the first portion 902 and the second portion 904 can be integrally formed together to form the strain relief hub 900 such that the first portion 902 and the second portion 904 are one continuous member.

Alternatively, the first portion 902 and the second portion 904 can be configured as two separate members to be attached to each other. When the second portion 904 is attached to the first portion 902, the second portion 904 can be tightened onto the first portion 902 and, consequently, can reduce an inner diameter of the first portion 902 to secure the wires, catheter, or other components passing through the strain relief hub 900 in place. The second portion 904 can be press fit onto the first portion 902 to tighten the first portion 902. Alternatively, or in addition, the first portion 902 can have a threaded end (not shown) and the second portion 904 can have a corresponding threaded end 916 such that the second portion 904 can be threadably attachable to the first portion 902. By tightening the second portion 904 onto the first portion 902, the first portion 902 and the second portion 904 can also form a water-tight seal with the components extending through the strain relief hub 900. For example, a gasket or other flexible material can be inserted between the strain relief hub 900 and the components passing through the strain relief hub 900 such that the first portion 902 can be tightened to form a water-tight seal. As another example, adhesive can be applied to the components passing through the strain relief hub 900 (e.g., at the aperture 906) to form a water-tight seal.

The second portion 904 can include a sloped end 918 to reduce sharp edges formed at the distal end of the strain relief hub 900. The sloped end 918 can be sloped from only a portion of the second portion 904 to the distal end, or the sloped end 918 can be sloped from the proximal end to the distal end of the second portion 904.

Figure 11A:
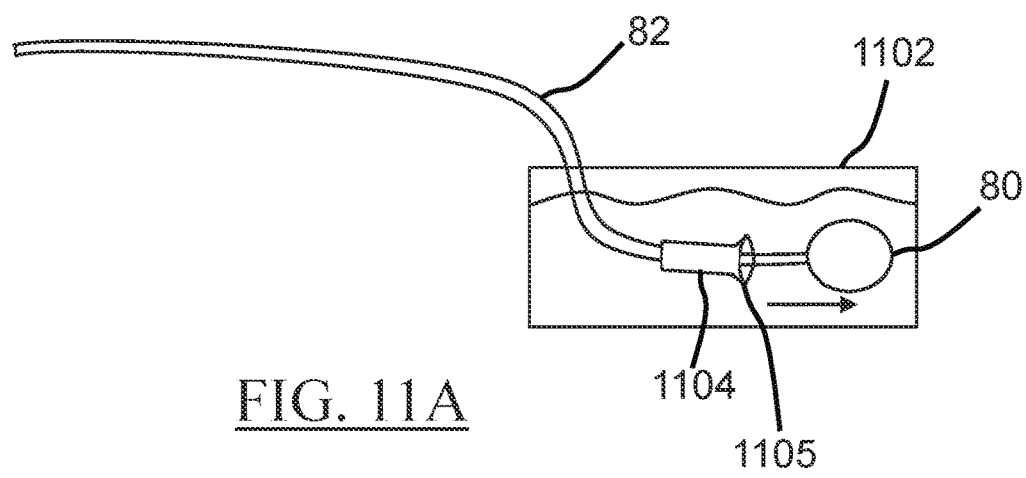
FIGS. 11A-11C are schematic pictorial illustrations of a balloon being prepared for a medical procedure, in accordance with the disclosed technology.
Figure 11B:
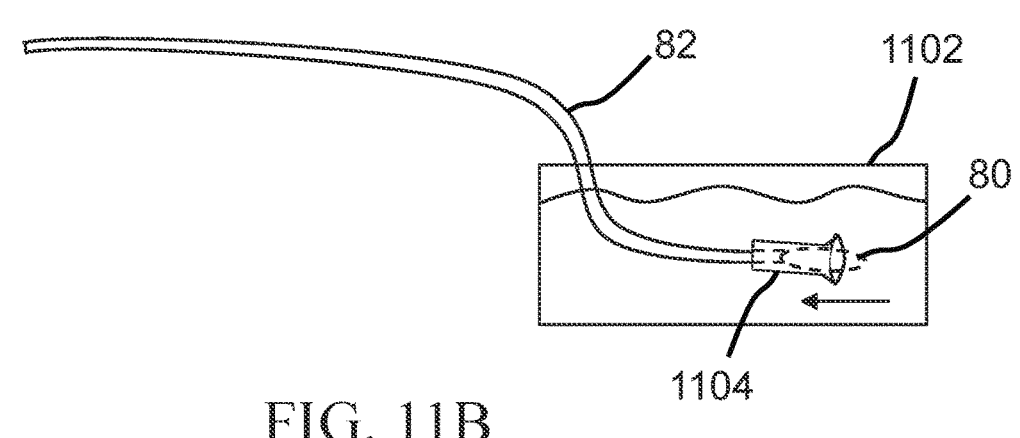
Figure 11C:
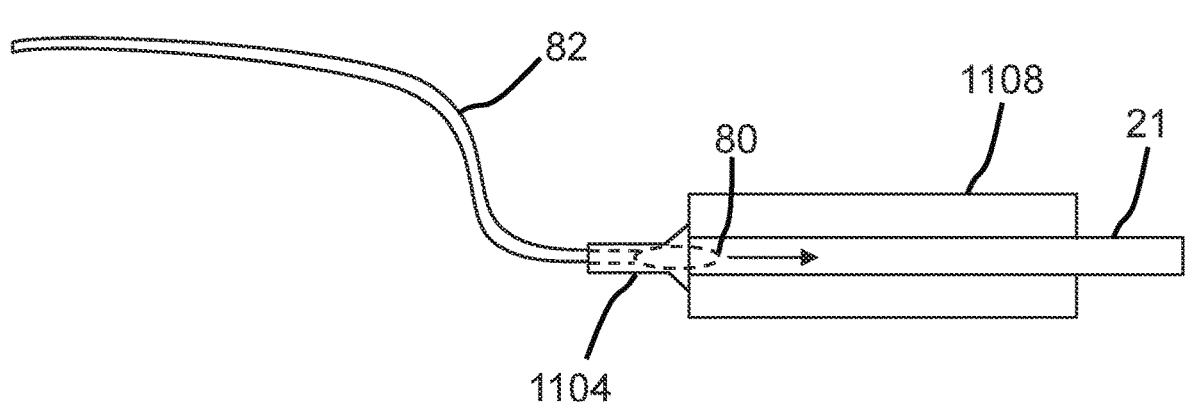

FIGS. 11A-11C are schematic pictorial illustrations of a balloon 80 being prepared for a medical procedure, in accordance with the disclosed technology. FIGS. 11A-11C can be understood in relation to the method illustrated and described in FIGS. 12A-12B, but a brief description of the various components is offered here for explanatory purposes.

Figure 12A:
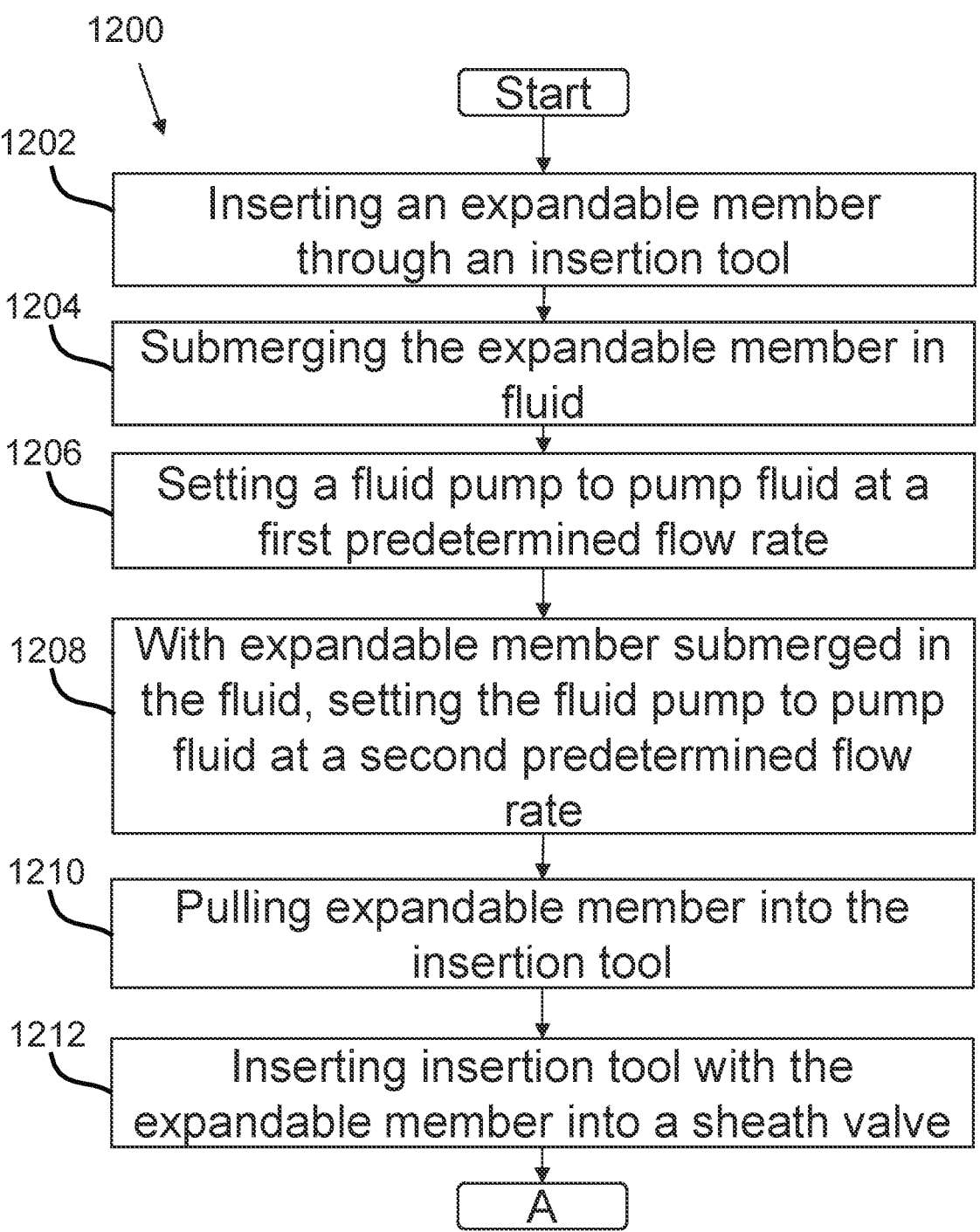

As illustrated in FIG. 12A, a balloon 80 attached to a shaft 82 can be inserted through an insertion tool 1104. As will be described, the insertion tool 1104 can be used to align and help facilitate insertion of the balloon 80 into a delivery sheath 21 to guide the balloon 80 to a patient's 18 heart. The balloon 80 can be submerged into a fluid bath 1102 of water or saline to help remove air or other gasses from the balloon 80. With the balloon 80 submerged, fluid (e.g., water or saline) can be pumped through the balloon 80 to further remove any air or gasses trapped in the balloon 80. With the balloon 80 still submerged, the balloon can be deflated and pulled into the insertion tool 1104 as illustrated in FIG. 11B.

With the balloon 80 still in the insertion tool 1104, the insertion tool 1104 can be coupled to a sheath valve 1108, aligned with the delivery sheath 21, and then pushed into the delivery sheath 21 to then be guided into the patient's 18 heart. To help facilitate easily pulling the balloon 80 into the insertion tool 1104 and then aligning the balloon 80 with the delivery sheath 21, the insertion tool 1104 can include a flared end 1105 at a distal end of the insertion tool 1104.

FIGS. 12A-12B are a flowchart illustrating a method 1200 of preparing an expandable member for a medical procedure as well as using the expandable member to perform the medical procedure, in accordance with the disclosed technology. The method 1200 can include inserting 1202 an expandable member (e.g., a balloon catheter, a basket catheter having spines, etc.) through an insertion tool (e.g., insertion tool 1104) and then submerging 1204 the expandable member in fluid (e.g., as illustrated in FIG. 11A). With the expandable member submerged in the fluid, the method 1200 can include setting 1206 a fluid pump to pump fluid at a first predetermined flow rate. With the expandable member still submerged in the fluid, the method 1200 can include setting 1208 the fluid pump to pump fluid at a second predetermined flow rate. The second flow rate can be less than the first flow rate. For example and not limitation, the first predetermined flow rate can be approximately 35 milliliters per minute (ml/min) while the second predetermined flow rate can be approximately 5 ml/min.

The method 1200 can include pulling 1210 the expandable member into the insertion tool (e.g., as illustrated in FIG. 11B) and then inserting 1212 the insertion tool with the expandable member at least partially into a sheath valve (e.g., as illustrated in FIG. 11C). Once the expandable member is aligned with a delivery sheath in the sheath valve, the expandable member is prepared and ready for performing a medical procedure in accordance with the examples disclosed herein.

Turning now to FIG. 12B, the method 1200 can include maneuvering 1214 the delivery sheath to a selected location. For example, the method 1200 can include maneuvering

1214 the delivery sheath to an area proximate the superior left pulmonary vein, the inferior left pulmonary vein, the superior right pulmonary vein, the inferior right pulmonary vein, or other locations within the patient's 18 heart or body as suitable for the particular medical procedure. The method 1200 can include pushing 1216 the expandable member until the expandable member is extended outside of the delivery sheath. The method 1200 can include setting 1218 the fluid pump to pump fluid at the first flow rate and then applying 1220 ablation energy to electrodes disposed on the expandable member until cardiac tissue is sufficiently ablated. As will be appreciated, the first flow rate can be a flow rate that is sufficient for irrigating and cooling the cardiac tissue during ablation. The fluid, for example, can be saline used for irrigating and cooling the cardiac tissue.

The method 1200 can include setting 1222 the fluid pump to pump fluid at the second flow rate and withdrawing 1224 the expandable member back to the delivery sheath. For example, once an operator 14 determines that cardiac tissue proximate the expandable member has been sufficiently ablated, the operator 14 can reduce the flow of the irrigation fluid by setting 1222 the fluid pump to pump fluid at the second flow rate such that the expandable member can be withdrawn 1224 back to the delivery sheath.

If the operator 14 determines that the medical procedure is completed, the method 1200 can include withdrawing 1226 the expandable member entirely from the delivery sheath. If, however, the operator 14 determines that the medical procedure is not yet completed, the method 1200 can include repeating elements 1214 through 1224 to perform ablation of cardiac tissue at other locations or at the same location again if the cardiac tissue was not sufficiently ablated the first time. As will be appreciated, the operator 14 can continue performing the ablation at various locations within the patient's 18 heart until the medical procedure is completed. Furthermore, as will be appreciated by one of skill in the art, the method 1200 can include any of the various features of the disclosed technology described herein and can be varied depending on the particular configuration. Thus, the method 1200 should not be construed as limited to the particular steps and order of steps explicitly described herein.

The embodiments described above are cited by way of example, and the present invention is not limited by what has been particularly shown and described hereinabove. Rather, the scope of the invention includes both combinations and sub combinations of the various features described hereinabove, as well as variations and modifications thereof which would occur to persons skilled in the art upon reading the foregoing description and which are not disclosed in the prior art.

What is claimed is:

1. A medical probe comprising:
a handle extending from a proximal portion to a distal portion;
a shaft extending from the distal portion of the handle and coupled to a proximal portion of a balloon disposed at a distal portion of the shaft;
a coupler disposed between the shaft and the proximal portion of the balloon, the coupler comprising:
a first portion having a first aperture disposed therethrough;
a second portion slidably coupled to the first portion and having a second aperture disposed therethrough and a spring recess; the second portion sized to be inserted at least partially into the first portion, the second portion configured to slide between a first position and a second position relative the first portion;

a vent port proximate a proximal end of the second portion, the vent port configured such that when the second portion is in the first position, the vent port is at least partially obstructed by the first portion, and when the second portion is in the second position, the vent port is unobstructed by the first portion; and a spring received by the spring recess in the first position to prevent the second portion from moving to the second position unless a predetermined force is applied to either the first portion or the second portion.

2. The medical probe according to claim 1, wherein the spring extends between the first portion and the second portion.

3. The medical probe according to claim 1, wherein the spring comprises a first spring, the medical probe further comprising a second spring, the second spring being disposed on a side of the coupler that is opposite the first spring, and the second portion comprises a second spring recess that receives the second spring in the first position.

4. The medical probe according to claim 1 further comprising a hollow tube disposed along a side of the second portion, wherein the vent port is disposed in the hollow tube.

5. The medical probe according to claim 4, wherein the hollow tube extends from approximately a distal portion of the second portion to approximately a distal end of the first portion.

6. The medical probe according to claim 5, wherein the hollow tube is configured to permit fluid to flow from the balloon of the medical probe when the second portion is in the second position.

7. The medical probe according to claim 1 wherein:

the first portion is sized to receive a sheath of the medical probe; and the second portion is size to be inserted at least partially into the balloon of the medical probe.

8. The medical probe according to claim 1, wherein the second portion further comprises a third aperture sized to receive a wire of an electrode assembly of the medical probe.

9. The medical probe according to claim 1, wherein the first aperture and the second aperture are axially aligned and sized to permit a catheter of the medical probe to pass therethrough.

10. The medical probe according to claim 1 wherein the second portion further comprises a raised end configured to prevent the second portion from decoupling from the first portion.

11. The medical probe of claim 1, further comprising an actuator shaft extending from the shaft to a distal portion of the balloon, the actuator shaft configured for movement along a longitudinal axis, and being coupled to a nose piece at the distal portion of the balloon, the nose piece being coupled to the distal portion of the balloon, the nose piece comprising:

a cylindrical body configured to be coupled to the distal portion of the balloon, the cylindrical body having:

an outer diameter of less than 0.14 inches; and an aperture extending therethrough from a proximal end of the cylindrical body to a distal end of the cylindrical body, the aperture sized to receive a catheter of the medical probe.

12. The medical probe according to claim 11, wherein the nose piece further comprises a ridge configured to form an interference fit with a coupler disposed proximate the distal portion of the balloon.

13. The medical probe according to claim 11, wherein the nose piece further comprises a second aperture extending therethrough from the distal portion of the cylindrical body to the proximal end of the cylindrical body, the second aperture configured to permit a fluid to pass therethrough from the balloon of the medical probe and out the distal end of the cylindrical body.

14. The medical probe of claim 1, further comprising a strain relief hub coupled to the handle, the strain relief hub comprising:

a first portion configured to be inserted at least partially into the handle of the medical probe, the first portion comprising a first aperture extending therethrough and a shoulder configured to interface with the handle of the medical probe to prevent the strain relief hub from sliding proximally or distally along the handle; and a second portion attached to the first portion and comprising a second aperture extending therethrough, the first aperture and the second aperture being axially aligned and configured to receive a catheter tube of the medical probe, the second portion having a smaller inner diameter than an inner diameter of the first portion.

15. The medical probe according to claim 14, wherein the first portion of the strain relief hub further comprises a recess extending approximately midway through the first portion and is configured to expose wires or a catheter extending through the strain relief hub.

\* \* \* \* \*